United States Patent [19]

Bajars et al.

[11] Patent Number: 4,658,074
[45] Date of Patent: Apr. 14, 1987

[54] CATALYTIC OXIDATIVE DEHYDROGENATION PROCESS

[75] Inventors: Laimonis Bajars, Princeton; Louis J. Croce, East Brunswick, both of N.J.

[73] Assignee: Petro-Tex Chemical Corporation, Houston, Tex.

[21] Appl. No.: 459,878

[22] Filed: May 28, 1965

[51] Int. Cl.$^4$ .............................. C07C 5/48; C07C 5/50
[52] U.S. Cl. .................................... 585/380; 585/443; 585/621; 585/658; 260/696
[58] Field of Search ...................... 260/696, 465.9, 680; 585/658, 662, 663, 380, 443, 621

[56] References Cited

U.S. PATENT DOCUMENTS

| | | | |
|---|---|---|---|
| 3,270,080 | 8/1966 | Christmann | 585/658 |
| 3,284,536 | 11/1966 | Bajars et al. | 260/683.3 |
| 3,303,234 | 2/1967 | Bajars et al. | 260/680 |
| 3,303,235 | 2/1967 | Croce et al. | 260/680 |
| 3,303,236 | 2/1967 | Croce et al. | 260/680 |
| 3,308,182 | 3/1967 | Gabliks et al. | 260/680 |
| 3,308,188 | 3/1967 | Bajars | 260/465.9 |
| 3,308,193 | 3/1967 | Bajars | 260/465.9 |
| 3,308,198 | 3/1967 | Bajars | 260/465.9 |
| 3,334,152 | 8/1967 | Bajars et al. | 260/680 |
| 3,342,890 | 9/1967 | Croce et al. | 585/658 |
| 3,577,354 | 5/1971 | Kehl | 252/468 |

Primary Examiner—Donald G. Daus
Assistant Examiner—Stephen M. Kapner
Attorney, Agent, or Firm—Kenneth H. Johnson

[57] ABSTRACT

Oxidative dehydrogenation of organic compounds in vapor phase with catalysts comprising crystalline compositions of iron, oxygen and at least one other metallic element. Preferred catalysts are ferrites.

32 Claims, No Drawings

CATALYTIC OXIDATIVE DEHYDROGENATION PROCESS

The catalysts of this invention contain iron, oxygen and at least one other metallic element. The catalysts are crystalline compositions of iron, oxygen, and at least one other metallic element. The catalysts may be ferrites and/or spinels. The metallic elements, other than iron, of the catalysts can be varied widely. For convenience, these metallic elements, other than iron, will be referred to as the second metallic ingredient(s). By this phrase is meant one or more metallic elements other than iron. Ordinarily, the ionic radius of the second metallic ingredient(s) is small enough that the oxygen anions are not spread too far apart. That is, the elements must be able to form a crystalline structure with the iron and oxygen.

The total number of atoms of the second metallic ingredient(s) should preferably be from about 0.05 to 2.0 total atoms per atom of iron and preferably will be from or about 0.20 to 1.0 total atoms per atom of iron, with a particularly preferred ratio of 0.35 to 0.6 total atoms per atom of iron.

A preferred type of catalyst of this type is that having a face-centered cubic form of crystalline structure. Examples of this type of catalyst are ferrites of the general formula $MeO \cdot Fe_2O_3$ where Me is a divalent metal cation such as $Mg^{++}$ or $Ni^{++}$. However, if the cations are large, such as $Sr^{++}$ (1.35 A.u.), the spinel structure may not occur and other types of ferrites having a hexagonal crystal of the type $SrO \cdot 6Fe_2O_3$ may be formed. Additional examples of hexagonal ferrites are $PbO \cdot 6Fe_2O_3$. These hexagonal ferrites are within the scope of the definition of catalysts of this invention.

The catalysts of this invention may be compositions having the metallic cations distributed in different manners in the crystalline structure. Thus, the second metallic ingredients may be arranged in the crystal either in "normal" or "inverse" arrangement. For instance, an example of a normal arrangement would be one wherein divalent cations are placed in tetrahedral sites and trivalent ions are in octahedral sites. An example of an inverse arrangement would be a structure where 8 trivalent ions are in tetrahedral sites and 8 trivalent ions and 8 divalent ions are in octahedral sites. Examples of ferrites having a normal arrangement are zinc ferrite and cadmium ferrite. However, the type of arrangement is influenced by temperature and high temperatures may cause at least a partial shift between inverse and normal structure. Therefore, catalysts having individual crystal structures intermediate between normal and inverse are common, and are within the scope of this invention. Also encompassed would be catalysts having a mixture or combination of crystals of different type. In fact, certain advantages may be obtained by having a combination of catalysts of the same composition but containing the atoms arranged in more than one structure.

Suitable catalysts may also be ferrites wherein other metals are partially substituted for the iron. For example, $Al^{+++}$ or $Cr^{+++}$ or other atoms having a valence of +3 may be partially substituted for some of the $Fe^{+++}$ atoms. Also, metal atoms having a valence of +4, such as $Ti^{++++}$ or $Ge^{++++}$ may replace some of the $Fe^{+++}$ ions. However, the catalysts will still suitably have iron present in an amount described above in relation to the total atoms of the second metallic ingredient(s). Thus, if the crystal contained, e.g., $Fe^{+++}$, $Cr^{+++}$, and $Mg^{++}$, the iron should still desirably be present within the ratios described, with the $Cr^{+++}$ and the $Mg^{++}$ being the second metallic ingredient(s) in this case.

It is not necessary that the catalysts contain all of the iron or the second metallic ingredient(s) in a crystalline structure. The catalysts may contain an excess of either iron or of the second metallic ingredient(s) over that which will form a crystalline structure. An example of this would be where magnesium ferrite contained or was combined with $Fe_2O_3$ or MgO. It is also possible for the defined ingredients to be partially present as interstitial components, or as substitutional components in solid solution with the normal crystalline structure, rather than being in the normal crystalline structure. For example, $Fe_2O_3$ and/or MgO may be in solid solution with magnesium ferrite. It is not necessary that the ingredients not contained in the crystalline structure be in solution with the crystalline structure as the catalysts may comprise a combination of crystals and/or solutions of other ingredients, and/or physical mixtures of other ingredients; this is true of ingredients either having the same or different composition as that of the crystal. Precipitates from solid solution may also be included in the catalyst. For example, it has been reported that ferrites of the type $MeFe_2O_4$, wherein Me is the second metallic ingredient(s), at high temperatures may form solid solutions with either of the components, $Fe_2O_3$ and MeO, such as from 15 to 75 percent by weight of $Fe_2O_3$ and from 25 to 85 percent by weight MeO, based on the weight of $MeFe_2O_4$. Solid solutions may be preserved by quenching from high temperatures and by other techniques.

The catalysts may have the iron combined in crystalline structure with oxygen and more than one other metallic element, as mentioned above. For example, a preferred type of ferrite is that essentially or approximately of the formula, $MeFe_2O_4$, where Me represents a divalent metal ion with an ionic radius approximately between 0.5 and 1.1 A.u., preferably between about 0.6 and 1.0 A.u. In the case of simple ferrites, Me may be, e.g., one of the divalent ions of the transition elements such as Mn, Co, Ni, Cu, Zn, Mg or Cd. However, a combination of these ions is also possible to form a ferrite such as $Ni_{0.5}Mg_{0.5}Fe_2O_4$ or $Ni_{0.25}Mg_{0.75}Fe_2O_4$. Moreover, the symbol Me may represent a combination of ions which have an average valency of two, for example, $Li_{0.5}Fe_{2.5}O_4$. However, it is essential that the crystalline structure contain a metallic element other than iron.

Examples of catalysts are such as magnesium ferrite, cobalt ferrite, nickel ferrite, cupric ferrite, cuprous ferrite, zinc ferrite, barium ferrite, strontium ferrite, manganese ferrite, lithium ferrite, calcium ferrite, cadmium ferrite, potassium ferrite, sodium ferrite, lead ferrite, silver ferrite, zirconium ferrite, and rare earth ferrites such as cerium ferrite, or mixtures of ferrites, such as ferrites containing iron combined with at least one element selected from the group consisting of Mg, Zn, Ni, Co, Mn, Cu, Cd, Ca, Ba, Sr. Al, Cr, Ti, V, Mo, W, Na, Li, K, Sn, Pb, Sb, Bi, Ga, Ce, Th, other rare earth elements and mixtures thereof. Examples of mixed ferrites are magnesium ferrite plus zinc ferrite, magnesium ferrite plus nickel ferrite, magnesium ferrite plus cobalt ferrite, magnesium ferrite plus nickel ferrite plus zinc ferrite, magnesium ferrite plus manganese ferrite. As explained above, these ferrites may be physical mixtures of the ferrites or may contain crystals wherein the different metallic atoms are contained in the same crystal; or a combination of physical mixtures and chemical combinations. Examples of chemical combinations would be magnesium zinc ferrite, calcium aluminatoferrite, calcium magnesium aluminoatoferrite, and so forth.

The valency of the metals in the catalysts do not have to be any particular values, although certain combinations are preferred or disclosed elsewhere. The determination of the valency of the ions is sometimes difficult and the results are uncertain. The different ions may exist in more than one valency state. For example, it is difficult to determine for $MnFe_2O_4$ whether the formula should be $Mn^{II}Fe_2^{III}O_4$ or $Mn^{III}Fe^{II}Fe^{III}O_4$. Another example is $Cu_{0.5}Fe_{2.5}O_4$ because the iron ions may be trivalent and the copper ion monovalent or on the other hand, this may be a mixed crystal of $Cu^{II}Fe_2O_4$ and $Fe^{II}Fe_2O_4$. However, a preferred catalyst is one which has the iron predominately in the $Fe^{+++}$ state. Examples of different types of iron compounds are the ferrates (II), such as $Na_2[Fe(OH)_4]$ and $Ba_2[Fe(OH)_6]$; ferrates III ("ferrites") such as $MgFe_2O_4$ or $Na_5[Fe(OH)_8]$ 4 $H_2O$ (although this compound might not be in this form under the conditions of reaction); ferrates IV (perferrites) such as strontium perferrites, barium perferrite, lithium perferrite; ferrates (VI) (ferrates) such as zinc ferrate, barium ferrate, sodium ferrate, copper ferrate and strontium ferrate; perferrates such as potassium, strontium, barium, sodium, manganese, lead, calcium and aluminum perferrate and mixtures thereof. Preferred compounds are the ferrites, particularly those having the spinel structure. Some ferrites are described in Ferromagnetism, by Richard M. Bozorth (D. Van Nostrand Co., Inc., 1951), which disclosure is hereby incorporated by reference.

Although the catalysts may be broadly defined as containing crystalline structures of iron, oxygen and the second metallic ingredient(s), certain types of catalysts are preferred. Valuable catalysts were produced comprising as the main active constituent in the catalyst surface exposed to the reaction gases, iron, oxygen and at least one element from Group IIA, IIB or VIII of the Periodic Table such as those selected from the group consisting of magnesium, manganese, calcium, cadmium, cobalt, zinc, nickel, barium, strontium, and mixtures thereof. The Periodic Table referred to is the one on pages 400–401 of the Handbook of Chemistry and Physics (39th edition, 1957-8, Chemical Rubber Publishing Co, Cleveland, Ohio). The preferred catalysts are the ferrites. Preferred catalysts will have iron in the catalyst surface in an amount from 20 to 95, and preferably from 30 to 90 weight percent of the total weight of iron and the second metallic ingredient(s). However, with the individual catalysts the ratio of iron to the other elements of Groups IIA, IIB and VIII will preferably be within certain ranges. For example, for magnesium catalysts, including magnesium ferrite, the catalysts will preferably have from 75 to 97 weight percent iron based on the total weight of iron and magnesium. Similarly, for the catalysts containing iron and one of the elements selected from the group consisting of calcium, cadmium and cobalt, the weight percent of iron will preferably be from 30 to 90 weight percent iron based on the total weight of iron and the calcium, cadmium and/or cobalt. For the zinc catalysts, including zinc ferrite, the weight percent iron will preferably be within the range of 20 to 95 weight percent with good results having been obtained with from about 51 to 80 weight percent iron based on the total weight of iron and zinc. For the catalyst containing strontium and/or barium, including strontium ferrite and barium including strontium ferrite and barium ferrite and mixtures thereof, the preferred weight percent of iron will be from 55 to 70 weight percent based on the total weight of iron and strontium and/or barium.

The preferred ferrites are the ferrites having a cubic face-centered configuration, such as the spinels. Ordinarily the ferrites will not be present in the most highly oriented crystalline structure, because it has been found that superior results may be obtained with catalysts wherein the crystalline structure of the ferrites is relatively disordered. The desired catalysts may be obtained by conducting the reaction to form the ferrite at relatively low temperatures, that is, at temperatures lower than some of the very high temperatures used for the formation of ferrites prepared for semi-conductor applications. Included in the definition of ferrites are the so-called intermediate oxides. Generally, the temperature of reaction for the formation of the catalysts comprising the particular ferrites will be less than 1300° C. and preferably less than 1150° C. The reaction time at the elevated temperature in the formation of the catalysts may preferably be from about 5 minutes to 4 hours at elevated temperatures high enough to cause formation of the ferrite but less than about 1150° C. Any iron not present in the form of the ferrite will desirably be present predominantly as gamma iron oxide. The alpha iron oxide will preferably be present in an amount of no greater than 40 weight percent of the catalytic surface, such as no greater than about 30 weight percent. The preferred catalysts will have as the most intense X-ray diffraction peak a peak within the range of 2.49 to 2.55, and more preferably a second most intense peak of from 1.44 to 1.52. The preferred catalysts will have surfaces generally having X-ray diffraction reflection peaks at d spacings within or about 4.79 to 4.89, 2.92 to 3.01, 2.48 to 2.57, 2.05 to 2.14, 1.67 to 1.75, 1.57 to 1.65, and 1.44 to 1.52, with the most intense peak being between 2.48 to 2.58. Suitable preferred ferrite catalysts are manganese ferrite with X-ray diffraction peaks within 4.87 to 4.94, 2.97 to 3.03, 2.53 to 2.59, 2.42 to 2.48, 2.09 to 2.15, 1.71 to 1.75, 1.62 to 1.66, 1.48 to 1.52, with the most intense peak being between 2.53 to 2.59; zinc ferrites having X-ray diffraction peaks within the d spacings 4.83 to 4.89, 2.95 to 3.01, 2.51 to 2.57, 2.40 to 2.46, 2.08 to 2.14, 1.69 to 1.75, 1.59 to 1.65, and 1.46 to 1.52, with the most intense peak being between 2.49 to 2.55; magnesium ferrites having peaks between 4.80 to 4.86, 2.93 to 2.99, 2.49 to 2.55, 2.06 to 2.12, 1.68 to 1.73, 1.58 to 1.63, and 1.45 to 1.50 with the most intense peak being between 2.49 to 2.55; and nickel ferrites having peaks within the d spacings of 4.79 to 4.85, 2.92 to 2.98, 2.48 to 2.54, 2.05 to 2.11, 1.57 to 1.63 and 1.44 to 1.49, with the most intense peak being within 2.48 to 2.54. The zinc ferrites will preferably have peaks within the d spacings 4.84 to 4.88, 2.96 to 3.00, 2.52 to 2.56, 2.41 to 2.45, 2.09 to 2.13, 1.70 to 1.74, 1.60 to 1.64, and 1.47 to 1.51, with the most intense peak of 2.52 to 2.56. Similarly, the magnesium ferrites will preferably have peaks within the d spacings of 4.81 to 4.85, 2.93 to 2.98, 2.50 to 2.54, 2.07 to 2.11, 1.69 to 1.72, 1.59 to 1.62, and 1.46 to 1.49, with the most intense peak being within the range of 2.50 to 2.54. The nickel ferrites will preferably have peaks within the d spacings 4.80 to 4.84, 2.93 to 2.97, 2.50 to 2.53, 2.07 to 2.10, 1.59 to 1.61, and 1.46 to 1.49, with the most intense peaks being within 2.50 to 2.53.

These X-ray determinations are suitably run with a cobalt tube.

The catalysts of this invention may also comprise phosphorus as an additive. The phosphorus should be present in an amount of from or about 0.2 to 16 weight percent phosphorus, based on the total weight of the atoms of iron and the second metallic ingredient(s).

One of the principal benefits obtained by the incorporation of phosphorus in the catalyst is the increased life of the catalyst. Of course, catalyst life is one of the most important criteria in the selection of catalysts. It has been found that the presence of phosphorus in critical amounts in the catalyst for some reason stabilizes the catalyst. The high initial yields obtained with the phosphorus modified catalyst are maintained for prolonged periods of time, and the catalysts have improved physical characteristics, such as attrition resistance.

The catalysts of this invention may also contain silicon as an additive. Silicon has also been found to be beneficial for increasing catalyst life and for maintaining high yields of products. Further advantages may be obtained in catalyst life and stability by incorporating both silicon and phosphorus in the catalyst.

The catalysts may be prepared in a number of ways. The ferrites, spinels, and so forth, of this invention may be prepared by known methods. The catalytic composition may be extruded into catalytic particles, compressed from dry ingredients, coated on a carrier, and so forth. The iron and at least one metal from the group consisting of the defined second metallic ingredient(s) may be incorporated using starting compounds such as oxides, nitrates, hydroxides, hydrates, oxalates, carbonates, acetates, halides, and so forth. Excellent catalysts are obtained by using salts of the elements. The catalysts of this invention will be used in the form of inorganic oxides for the dehydrogenation reaction. This definition means that the catalysts are inorganic and contain oxygen; included in this definition are the ferrites. However, as pointed out, the catalysts may be produced from organic precursors such as the acetates or oxalates, and the crystalline structure may be formed in situ during the dehydrogenation reaction.

The silicon, phosphorus, or other additives may be added at any stage of the catalyst preparation, but it generally will be added in such amount that intimate mixing with the other ingredients is insured. One suitable method of preparation of silicon containing catalysts is to add the silicon in the form of silica, $SiO_2$. Silica may be incorporated in the catalyst, for example, by the acid hydrolysis of an organic or inorganic silicate, such as tetraethyl ortho silicate or sodium silicate. The resulting hydrogel may be slurried with the other catalytic ingredients. If the starting material is a silicate salt such as sodium silicate, ordinarily the solution formed by acid hydrolysis will be filtered and washed to remove extraneous ions before combining with the other catalytic compositions. Another method of preparation is to mix a silicate, ferrite or ferrite precursors in aqueous media whereby the silicate hydrolyzes in the presence of the other components of the catalyst. The silicon may also be added as finely ground and dried silica which may be added to the other components of the catalyst. Regardless of the method of preparation, the silicon should be present in an intimate combination with the other catalytic components such as iron and at least one other metal element.

Similarly, if phosphorus is included in the catalyst, the phosphorus may be added in a variety of ways. One method is to mix the dry ingredients, other than the phosphorus, with a phosphorus compound such as phosphoric acid or an ammonium phosphate solution and thereafter extrude the damp powder. The ingredients may be dry mixed and compressed into tablets. If the iron is present in the preferred manner, that is, predominantly as a ferrite, the ferrite may be formed in situ on a carrier and the phosphorus added at various stages of the preparation. However, one of the preferred catalysts is a catalyst in the form of unsupported catalyst particles, such as extruded cylindrical pellets.

The process of this invention may be applied to the dehydrogenation of a great variety of organic compounds to obtain the corresponding unsaturated derivative thereof. Such compounds normally will contain from 2 to 20 carbon atoms, at least one

grouping, a boiling point below about 350° C., and such compounds may contain other element, in addition to carbon and hydrogen such as oxygen, halogens, nitrogen and sulphur. Preferred are compounds having from 2 to 12 carbon atoms, and especially preferred are compounds of 2 to 6 carbon atoms.

Among the types of organic compounds which are successfully dehydrogenated to the corresponding unsaturated derivative by means of the novel process of this invention are nitriles, amines, alkyl halides, ethers, esters, aldehydes, ketones, alcohols, acids, alkyl aromatic compounds, alkyl heterocyclic compounds, cycloalkanes, alkanes, alkenes, and the like. Illustrative dehydrogenations include propionitrile to acrylonitrile, propionaldehyde to acrolein, ethyl chloride to vinyl chloride, methyl isobutyrate to methyl methacrylate, 2,3 dichlorobutane to chloroprene, ethyl pyridine to vinyl pyridine, ethylbenzene to styrene, isopropylbenzene to α-methyl styrene, ethylcyclohexane to styrene, cyclohexane to benzene, ethane to ethylene, propane to propylene, isobutane to isobutylene, n-butane to butene and butadiene-1,3, butene to butadiene-1,3, n-butane to vinyl acetylene, methyl butene to isoprene, cyclopentane to cyclopentene and cyclopentadiene-1,3, n-octane to ethyl benzene and ortho-xylene, monomethylheptanes to xylenes, propane to propylene to benzene, ethyl acetate to vinyl acetate, 2,4,4-trimethylpentane to xylenes, and the like. This invention is useful for the formation of new carbon to carbon bonds by the removal of hydrogen atoms such as the formation of a carbocyclic compound from two aliphatic hydrocarbon compounds or the formation of a dicyclic compound from a monocyclic compound having an acyclic group. Examples of conversions are the conversion of n-heptane to toluene and propene to diallyl. Representative materials which are dehydrogenated by the novel process of this invention include ethyl toluene, alkyl chlorobenzenes, ethyl naphthalene, isobutyronitrile, propyl chloride, isobutyl chloride, ethyl fluoride, ethyl bromide, n-pentyl iodide, ethyl dichloride, 2,3 dichlorobutane, 1,3 dichlorobutane, 1,4 dichlorobutane, the chlorofluoroethanes, methyl pentane, methylethyl ketone, diethyl ketone, n-butyl alcohol, methyl propionate, and the like. This invention is particularly adapted to the preparation of vinylidene compounds containing at least one

group, that is, a group containing a terminal methylene group attached by a double bond to a carbon atom, and having 2 to 12 carbon atoms by the dehydrogenation of compounds of the formula $CH_3—CH_2—R$ wherein R is an organic radical of from 0 to 10 carbon atoms, preferably a hydrocarbon. Similarly, acetylenic compounds of the formula $CH\equiv C—$ may be produced from the same starting materials.

Preferably oxygen is employed, suitably in an amount within the range of 0.2 to about 5.0 mols of oxygen per mol of organic compound to be dehydrogenated, preferably from 0.2 to 2.5 mols per mol. Generally, better results may be obtained if the oxygen concentration is maintained between about 0.25 and about 1.6 mols of oxygen per mol of organic compound to be dehydrogenated, such as between 0.35 and 1.2 mols of oxygen. The oxygen may be fed to the reactor as pure oxygen, as air, as oxygen-enriched air, oxygen mixed with diluents, and so forth. Based on the total gaseous mixture entering the reactor, good results are obtained with oxygen present in an amount from about 0.5 to 25 volume percent of the total gaseous mixture, such as in an amount from about 1 to 15 volume percent of the total. The total amount of oxygen utilized may be introduced into the gaseous mixture entering the catalytic zone or sometimes it has been found desirable to add the oxygen in increments, such as to different sections of the reactor. The above described proportions of oxygen employed are based on the total amount of oxygen used. The oxygen may be added directly to the reactor or it may be premixed, for example, with a diluent or steam.

It is one of the advantages of this invention that halogen may also be added to the reaction gases to give excellent results. The addition of halogen to the feed is particularly effective when the hydrocarbon to be dehydrogenated is saturated. The halogen fed to the dehydrogenation zone may be either elemental halogen or any compound of halogen which would liberate halogen under the conditions of reaction. Suitable sources of halogen are such as hydrogen iodide, hydrogen bromide and hydrogen chloride; aliphatic halides, such as ethyl iodide, methyl bromide, 1,2-dibromo ethane, ethyl bromide, amyl bromide, and allyl bromide; cycloaliphatic halides, such as cyclohexylbromide; aromatic halides, such as benzyl bromide; halohydrins, such as ethylene bromohydrin; halogen substituted aliphatic acids, such as bromoacetic acid; ammonium iodide; ammonium bromide; ammonium chloride; organic amine halide salts, such as methyl amine hydrobromide; and the like. Mixtures of various sources of halogen may be used. The preferred sources of halogen are iodine, bromine, and chlorine, and compounds thereof such as hydrogen bromide, hydrogen iodide, hydrogen chloride, ammonium bromide ammonium iodide, ammonium chloride, alkyl halides of one to six carbon atoms and mixtures thereof, with the iodine and bromine compounds being particularly preferred and the best results having been obtained with ammonium iodide, bromide, or chloride. When terms such as halogen liberating materials or halogen materials are used in the specification and claims, this includes any source of halogen such as elemental halogens, hydrogen halides, or ammonium halides. The amount of halogen, calculated as elemental halogen, may be as little as about 0.0001 or less mol of halogen per mol of the organic compound to be dehydrogenated to as high as 0.2 or 0.5. The preferred range is from about 0.001 to 0.09 mol of halogen per mol of the organic compound to be dehydrogenated.

The temperature for the dehydrogenation reaction generally will be at least about 250° C., such as greater than about 300° C. or 375° C., and the maximum temperature in the reactor may be about 650° C. or 750° C. or perhaps higher under certain circumstances. However, excellent results are obtained within the range of or about 300° C. to 575° C., such as from or about 325° C. to or about 525° C. The temperatures are measured at the maximum temperature in the reactor. An advantage of this invention is that lower temperature of dehydrogenation may be utilized than are possible in conventional dehydrogenation processes. Another advantage is that large quantities of heat do not have to be added to the reaction as was previously required.

The dehydrogenation reaction may be carried out at atmospheric pressure, superatmospheric pressure or at sub-atmospheric pressure. The total pressure of the system will normally be about or in excess of atmospheric pressure, although sub-atmospheric pressure may also desirably be used. Generally, the total pressure will be between about 4 p.s.i.a. and about 100 or 125 p.s.i.a. Preferably, the total pressure will be less than about 75 p.s.i.a. and excellent results are obtained at about atmospheric pressure.

The initial partial pressure of the organic compound to be dehydrogenated will preferably be equivalent to equal to or less than one-half atmosphere at a total pressure of one atmosphere. Generally, the combined partial pressure of the organic compound to be dehydrogenated, together with the oxygen, will also be equivalent to less than one-half atmosphere at a total pressure of one atmosphere. Preferably, the initial partial pressure of the organic compound to be dehydrogenated will be equivalent to no greater than one-third atmosphere or no greater than one-fifth atmosphere at a total pressure of one atmosphere. Also, preferably, the initial partial pressure of the combined organic compound to be dehydrogenated plus the oxygen will be equivalent to no greater than one-third or no greater than one-fifth atmosphere at a total pressure of one atmosphere. Reference to the initial partial pressure of the organic compound to be dehydrogenated means the partial pressure of the organic compound as it first contacts the catalytic particles. An equivalent partial pressure at a total pressure of one atmosphere means that one atmosphere total pressure is a reference point and does not imply that the total pressure of the reaction must be operated at atmospheric pressure. For example, in a mixture of one mol of ethyl chloride, three mols of steam, and one mol of oxygen under a total pressure of one atmosphere, the ethyl chloride would have an absolute pressure of one-fifth of the total pressure, or roughly six inches of mercury absolute pressure. Equivalent to this six inches of mercury-ethyl chloride absolute pressure at atmospheric pressure would be ethyl chloride mixed with oxygen under a vacuum such that the partial pressure of the ethyl chloride is 6 inches of mercury absolute. The combination of a diluent such as nitrogen, together with the use of a vacuum, may be utilized to achieve the desired partial pressure of the organic compound. For the purpose of this invention, also equivalent to the six inches of mercury ethyl chloride absolute pressure at atmospheric pressure would be the same mixture of one mol of ethyl chloride, three mols of steam, and one mol of oxygen under a total pressure greater than atmospheric, for example, a total pressure of 20 p.s.i.a. Thus, when the total pressure in the reaction zone is greater than one atmosphere, the absolute values for the pressure of the organic compound to be dehydrogenated will be increased in direct proportion to the increase in total pressure above one atmosphere.

The partial pressures described above may be maintained by the use of diluents such as nitrogen, helium or other gases. Conveniently, the oxygen may be added as air with the nitrogen acting as a diluent for the system. Mixtures of diluents may be employed. Volatile compounds which are not dehydrogenated or which are dehydrogenated only to a limited extent may be present as diluents.

Preferably, the reaction mixture contains a quantity of steam, with the range generally being between about 2 and 40 mols of steam per mol of organic compound to be dehydrogenated. Preferably, steam will be present in an amount from about 3 to 35 mols per mol of organic compound to be dehydrogenated and excellent results have been obtained within the range of about 5 to about 30 mols of steam per mol of organic compound to be dehyddrogenated. The functions of the steam are several-fold, and the steam may not merely act as a diluent. Diluents generally may be used in the same quantities as specified for the steam. Excellent results are obtained when the gaseous composition fed to the reactor consists essentially of the organic compound to be dehydrogenated, inert diluents, and oxygen as the sole oxidizing agent.

The gaseous reactants may be conducted through the reaction chamber at a fairly wide range of flow rates. The optimum flow rate will be dependent upon such variables as the temperature of reaction, pressure, particle size, and whether a fluid bed or fixed bed reactor is utilized. Desirable flow rates may be established by one skilled in the art. Generally, the flow rates will be within the range of about 0.10 to 25 liquid volumes of the organic compound to be dehydrogenated per volume of reactor containing catalyst per hour (referred to as LHSV), wherein the volumes of organic compound are calculated at standard conditions of 0° C. and 760 mm. of mercury. Usually, the LHSV will be between 0.15 and about 5 or 10. For calculation, the volume of reactor containing catalyst is that volume of reactor space including the volume displaced by the catalyst. For example, if a reactor has a particular volume of cubic feet of void space, when that void space is filled with catalyst particles, the original void space is the volume of reactor containing catalyst for the purpose of calculating the flow rate. The gaseous hourly space velocity (GHSV) is the volume of the organic compound to be dehydrogenated in the form of vapor calculated under standard conditions of 0° C. and 760 mm. of mercury per volume of reactor space containing catalyst per hour. Generally, the GHSV will be between about 25 and 6400, and excellent results have been obtained between about 38 and 3800. Suitable contact times are, for example, from about 0.001 or higher to about 4 to 10 or 20 seconds, with particularly good results being obtained between 0.01 and 5 seconds. The contact time is the calculated dwell time of the reaction mixture in the reaction zone, assuming the mols of product mixture are equivalent to the mols of feed mixture. For the purpose of calculation of contact times, the reaction zone is the portion of the reactor containing catalyst which is at a temperature of at least 250° C.

The catalytic surface described in the surface which is exposed in the dehydrogenation zone to the reactor; that is, if a catalyst carrier is used, the composition described as a catalyst refers to the composition of the surface and not to the total composition of the surface coating plus carrier. Catalyst binding agents or fillers may be used, but these will not ordinarily exceed about 50 percent or 60 percent by weight of the catalytic surface. These binding agents and fillers will preferably be essentially inert. Preferred catalysts are those that have as a catalytic surface exposed to the reaction gases at least 25 or preferably 50 weight percent of the defined catalytic surface. Also preferably iron will constitute at least 50 atomic weight percent of the cations in the catalytic surface. Suitable catalysts are those which do not contain sodium or potassium as an additive in the crystal structure, such as those containing less than 5 or less than 2 percent by weight of sodium or potassium based on the total weight of the catalyst. This is particularly true for processes that do not utilize halogen in the gaseous feed to the reactor.

The catalyst will by definition be present in a catalytic amount. The amount of catalyst will ordinarily be present in an amount greater than 10 square feet of catalyst surface per cubic foot of reaction zone containing catalyst. Of course, the amount of catalyst may be much greater, particularly when irregular surface catalysts are used. When the catalyst is in the form of particles, either supported or unsupported, the amount of catalyst surface may be expressed in terms of the surface area per unit weight of any particular volume of catalyst particles. The ratio of catalytic surface to weight will be dependent upon various factors, including the particle size, particle size distribution, apparent bulk density of the particles, amount of active catalyst coated on the carrier, density of the carrier, and so forth. Typical values for the surface to weight ratio are such as about one-half to 200 square meters per gram, although higher and lower values may be used.

The dehydrogenation reactor may be of the fixed bed or fluid bed type. Conventional reactors for the production of unsaturated organic compounds by dehydrogenation are satisfactory. Excellent results have been obtained by packing the reactor with catalyst particles as the method of introducing the catalytic surface. The catalytic surface may be introduced as such or it may be deposited on a carrier by methods known in the art such as by preparing an aqueous solution or dispersion of a catalytic material and mixing the carrier with the solution or dispersion until the active ingredients are coated on the carrier. If a carrier is utilized, very useful carriers are silicon carbide, aluminum oxide, magnesia, pumice, and the like. Other known catalyst carriers may be employed. When carriers are used, the amount of catalyst on the carrier will suitably be between about 5 to 75 weight percent of the total weight of the active catalytic material plus carrier. Another method for introducing the required surface is to utilize as a reactor a small diameter tube wherein the tube wall is catalytic or is coated with catalytic material. Other methods may be utilized to introduce the catalytic surface such as by the use of rods, wires, mesh, or shreds, and the like, of catalytic material.

According to this invention, the catalyst may be autoregenerative and the process may be continuous. Moreover, small amounts of tars and polymers are formed as compared to some prior art processes.

In the following examples will be found specific embodiments of the invention and details employed in the practice of the invention. Percent conversion refers to the mols of organic compound to be dehydrogenated that is consumed, based on the mols of the said organic compound fed to the reactor, percent selectivity refers to the mols of product formed based on the mols of the said organic compound consumed, and percent yield refers to the mols of product formed based on the mols of the said organic compound fed.

EXAMPLE 1

A nickel ferrite catalyst is prepared from 37.4 grams of nickelous oxide, 79.9 grams ferric oxide and 74.6 grams of potassium chloride. The dry ingredients are mixed thoroughly and then reacted at 900° C. for a period of 1½ hours. After cooling to room temperature, hot distilled water is used to extract the potassium chloride from the reacted mixture. A highly magnetic dark brown solid is obtained after the reaction mixture is dried in an oven at 110° C. The product is found to be nickel ferrite by X-ray diffraction analysis.

The nickel ferrite is coated on 4 to 5 mesh alumina supports (Carborundum Company type AMC). Propionitrile is dehydrogenated at atmospheric pressure in a Vycor* glass reactor (36"×1" O.D.) having a 35 cc. catalyst bed. The remainder of the reactor was filled with ¼"×¼" Vycor Raschig rings. Propionitrile, oxygen, and steam are introduced into an adapter located on top of the glass reactor, and the effluent gases are passed through a cold water condenser to remove most of the steam. Samples of the effluent gases are withdrawn with a syringe at the exit from the condenser. They are analyzed in a vapor chromatograph. The temperature inside the reactor is measured by a type J iron-constantan thermocouple enclosed in a 7 mm. O.D. Vycor tubing thermocouple well. The oxygen is fed as C.P. oxygen, 99.5 mol percent minimum oxygen.

*Vycor is the tradename of Corning Glass Works, Corning, N.Y., and is composed of approximately 96 percent silica with the remainder being essentially $B_2O_3$.

The propionitrile, oxygen, and steam are fed to the reactor in an amount of 0.6 mol of oxygen per mol of propionitrile and 30 mols of steam per mol of propionitrile. The liquid hourly space velocity is 10 (with the calculation being based on the volume of the reactor containing catalyst, that is, the 35 cc. catalyst section). The acrylonitrile product is recovered from the reactor effluent.

An X-ray diffraction pattern is obtained on the catalyst of Example 1. The powder pattern is obtained using a Norelco constant potential diffraction unit, type number 12045, equipped with a wide range goniometer type no. 42202, chromium tube type no. 32116, geiger counter type no. 34473; all coupled to the Norelco circuit panel type no. 12049. The chromium K alpha radiation is supplied by operating the tube at a constant potential of 40 kilovolts and a current of 10 milliamperes. A vanadium filter is used to remove K beta radiation. The geiger tube detector is operated at 1575 volts. A 1° divergence, 0.006 inch receiving, and 1° scatter slits are used. Strip chart recordings used for identification were made with a scanning speed of 1° 2 theta per minute with a chart speed of ½ inch per minute. A time constant of 2 seconds and a full scale chart reading of 100 counts per second are used. Under the above conditions, the patterns noted below are found. The values of $I/I_1$ noted are those for $NiFe_2O_4$. A small amount of alpha-$Fe_2O_3$ is found in the patterns. The data is reported in the Table.

TABLE

| D | $I/I_1$ |
|---|---|
| 4.82 | 14 |
| 2.948 | 31 |
| 2.698 | weak |
| 2.513 | 100 |
| 2.406 | 13 |
| 2.082 | 23 |
| 1.702 | 10 |
| 1.606 | 24 |
| 1.474 | 40 |
| 1.453 | weak |
| 1.318 | 4 |

EXAMPLE 2

The general procedure of Example I is repeated for the dehydrogenation of propionitrile to acrylonitrile with the exception that potassium chloride is omitted in the formation of the nickel ferrite.

EXAMPLE 3

A nickel ferrite catalyst is prepared from nickel carbonate and hydrated yellow ferric iron oxide. The ratio of ingredients is such that there are two atoms of iron per atom of nickel. The nickel carbonate and iron oxide are thoroughly mixed in an aqueous slurry and the slurry thereafter dried. The dry cake is broken into lumps and a 4 to 8 mesh fraction is reacted for 30 minutes at 950° C. to form the nickel ferrite. The catalyst is evaluated for the dehydrogenation of 2-chlorobutane to chloroprene. A stainless steel reactor one inch in diameter is used and 20 cc. of the 4 to 8 mesh catalyst is utilized. 30 mols of steam and 0.6 mol of $O_2$ (fed as air) are fed per mol of 2-chlorobutane. The flow rate of 2-chlorobutane is 1.0 LHSV. Chloroprene is produced at a reactor temperature of 425° C.

EXAMPLE 4

Example 3 is repeated for the dehydrogenation of 2-chlorobutane to chloroprene, with the exception that the catalyst contains 2.5 atoms of iron per atom of nickel.

EXAMPLE 5

Example 3 is repeated with the exception that the catalyst contains 1.67 atoms of iron per atom of nickel and the amount of oxygen is increased to 0.75 mol of $O_2$ per mol of 2-chlorobutane fed.

EXAMPLE 6

The procedure of Example 1 is repeated for the dehydrogenation of isobutyronitrile using the catalyst of Example 1. Additionally, 0.03 mol of bromine (fed as an aqueous solution of HBr) per mol of isobutyronitrile is fed to the reactor. Oxygen is fed at rate of 0.85 mol of $O_2$ per mol of isobutyronitrile and steam is employed in a ratio of 15 mols of steam per mol of isobutyronitrile fed. The flow rate of isobutyronitile is 10 LHSV. Methacrylonitrile is obtained in good yields at a reactor temperature of 450° C.

When an equivalent amount of iodine and chlorine are substituted for the bromine in Example 6, excellent yields of methacrylonitrile are obtained.

EXAMPLE 7

Zinc ferrite (Columbian Carbon Company EG-2, having about 32.6 to 32.8 weight percent zinc calculated as zinc oxide) particles are packed in the reactor described in Example 1. The catalyst bed is 50 cc. in volume. A mixture of methyl isopropyl ketone, oxygen and steam are fed to the reactor in an amount of 0.5 mol of oxygen per mol of methyl isopropyl ketone and 20 mols of steam per mol of methyl isopropyl ketone. The methyl isopropyl ketone is fed at a rate of 1.0 LHSV. At a reactor temperature of 425° C., methyl isopropenyl ketone is produced.

EXAMPLES 8 TO 22

200 gr. of Columbian Carbon Company magnesium ferrite EG-1 is slurried into a thick paste using 320 cc. of distilled water. The paste is dried in an oven at 140° C. for 1½ hours, and then broken into small granules. A 6 to 8 mesh fraction of this broken catalyst is used as the catalyst for these Examples. The reactor used is a 1-inch diameter I.P.S. 316 stainless steel reactor, which is 24 inches long. Into the bottom of the reactor is loaded 100 cc. of the 6 to 8 mesh magnesium ferrite catalyst particles, and on top of this catalyst is added 6 mm.×6 mm. Vycor Raschig rings to fill the remainder of the reactor and to act as a preheat zone. The various compounds are dehydrogenated by feeding a mixture of the compound to be dehydrogenarted, any diluent, and air over the magnesium ferrite catalyst under the conditions listed.

An X-ray diffraction pattern is made of the magnesium ferrite catalyst prior to use in these examples. The powder diffraction patterns are made with a Norelco constant potential diffraction unit type no. 12215/0 equipped with a wide range goniometer type no. 42273/0, cobalt tube type no. 32119, proportional counter type no. 52250/1; all coupled to the Norelco circuit panel type no. 12206/53. The cobalt K alpha radiation is supplied by operating the tube at a constant potential of 30 kilovolts and a current of 10 milliamperes. An iron filter is used to remove K beta radiation. The detector voltage is 1660 volts and the pulse height analyzer is set to accept pulses with amplitudes between 10 and 20 volts only. Slits used are divergence 1°, receiving 0.006 inches and scatter 1°. Strip chart recordings for identification are made with a scanning speed of ¼° per minute, time constant of 4 seconds and a full scale at $10^8$ counts per second. Under these conditions, the following X-ray diffraction is obtained:

| d    | $I/I_1$   |
|------|-----------|
| 4.82 | 9         |
| 3.67 | very weak |
| 2.96 | 32        |
| 2.69 | about 7   |
| 2.53 | 100       |
| 2.21 | very weak |
| 2.09 | 28        |
| 1.84 | very weak |
| 1.71 | 10        |
| 1.69 | very weak |
| 1.61 | 30        |
| 1.48 | 60        |

Using the magnesium ferrite catalyst, the following runs are made:

| Example | Feed | Flow Rate LHSV | Max. Temp. °C. | Gaseous Additive[1] | Oxygen[2] | Product |
|---|---|---|---|---|---|---|
| 8  | Propionaldehyde    | 1.0  | 425 | 15 steam    | 0.6  | Acrolein |
| 9  | Cyclohexane        | 1.5  | 450 | 10 steam    | 1.0  | Benzene |
| 10 | Ethyl Chloride     | 1.0  | 450 | 15 helium   | 1.0  | Vinyl Chloride |
| 11 | 2 chloro-butane-2  | 0.5  | 425 | 20 steam    | 0.8  | Chloroprene |
| 12 | Propionitrile      | 1.0  | 400 | 15 steam    | 0.75 | Acrylonitrile |
| 13 | Ethyl benzene      | 1.0  | 450 | 15 nitrogen | 0.75 | Styrene |
| 14 | Ethyl cyclohexane  | 2.0  | 450 | 15 nitrogen | 0.75 | Styrene |
| 15 | 2,3-dichlorobutane | 1.0  | 450 | 20 steam    | 0.75 | Chloroprene, 2-chloro-butene-2 |
| 16 | n-Butane           | 1.0  | 525 | 20 steam    | 0.75 | Butene-1, Butadiene-1,3 Vinyl acetylene |
| 17 | Isobutyronitrile   | 1.0  | 475 | 20 steam    | 0.75 | Methacrylonitrile |
| 18 | Isopropyl benzene[3] | 1.25 | 450 | —         | 0.75 | Methyl styrene |
| 19 | Methyl isobutyrate | 1.0  | 425 | 15 nitrogen | 0.75 | Methyl methacrylate |
| 20 | Ethyl pyridine     | 1.0  | 450 | 15 nitrogen | 0.5  | Vinyl pyridine |
| 21 | 1-Bromo propane    | 1.0  | 425 | 15 steam    | 2.0  | 1-Bromo propene-1 |
| 22 | 2-Methyl butane    | 1.0  | 450 | 2 steam     | 2.0  | Isoprene |

[1]Per mol of the compound to be dehydrogenated.
[2]Mols of oxygen per mol of the compound to be dehydrogenated (fed as air, but calculated as mols of $O_2$).
[3]Operated under vacuum to give a partial pressure of isopropyl benzene of 3 inches of mercury absolute.

EXAMPLE 23

A catalyst comprising zinc ferrite is formed from ½ mol of ZnO and one mol of $Fe_2O_3$. The dry metal oxides are thoroughly mixed prior to the reaction to form the zinc ferrite. Zinc ferrite is formed by reacting the combination of oxides at 850° C. Ethyl chloride is dehydrogenated to vinyl chloride utilizing 0.5 mol of oxygen per mol of ethyl chloride together with 25 mols of steam per mol of ethyl chloride. The flow rate is 1.5 LHSV and the catalyst volume is 50 cc. The maximum temperature in the reactor is 450° C.

EXAMPLE 24

A zinc ferrite catalyst is formed from iron nitrate and zinc nitrate. The nitrates are used in a ratio equivalent to 0.55 mol of $Fe_2O_3$ and 0.45 mol of ZnO. The catalytic composition is deposited on an inert cylindrical carrier. After the nitrates are decomposed, the zinc ferrite is formed by reacting the composition at 800° C. for sixty minutes. Utilizing a flow rate of 1.0 LHSV, a steam ratio of 30 mols and an oxygen ratio of 0.75 mol of oxygen per mol of butene-2, butene-2 is dehydrogenated to butadiene at a reactor temperature of 450° C. at a conversion of 60 mol percent and a selectivity of 92 mol percent to give a yield of butadiene of 55 mol percent.

EXAMPLE 25

Example 24 is repeated with the exception that the catalytic composition is reacted at 850° C. for 20 minutes instead of 800° C. for sixty minutes. At a reactor temperature of 450° C., 70 mol percent of the butene-2 is converted at a selectivity of 92 mol percent to give a yield of 64 mol percent of butadiene-1,3.

EXAMPLE 26

Example 25 is repeated with the exception that iron nitrate and zinc nitrate are used in amounts equivalent to 0.45 mol of $Fe_2O_3$ per 0.55 mol of ZnO. The yield of butadiene-1,3 is 62 mol percent.

EXAMPLE 27

Example 25 is repeated with the exception that the catalytic composition is formed by reacting at 700° C. for a period of 60 minutes. The yield of butadiene-1,3 is 69 mol percent.

EXAMPLE 28

236 gr. of $Fe(NH_4)_2(SO_4)_2.6H_2O$ and 86 gr. $Mg(NO_3)_2.6H_2O$ are dissolved in 1000 ml. of distilled water. 142 gr. of $(NH_4)_2C_2O_4.H_2O$ are dissolved in 2000 ml. of distilled water. The two solutions are mixed at 35° C. while stirring. The resulting yellow precipitate of ferrous and magnesium oxalate is filtered, washed, and dried 16 hours at 100° C. The dried precipitate is reacted by heating for 4 hours at 950° C. and thereafter ground to sub 325 mesh.

A supported catalyst is then made by coating this material on 6 to 8 mesh inert support (Carborundum Company's polysurface fused alumina). The catalyst has 30 weight percent actives. 20 cc. of this catalyst is loaded in a 1-inch O.D. stainless steel tube, 16 inches long. The catalyst bed is supported by 20 cc. of Alcoa $\frac{1}{8}''$ T-162 fused alumina spheres, and the remainder of the reactor tube is also filled with these spheres.

Butene-2 is dehydrogenated by feeding a mixture of butene-2 and air over the catalyst comprising magnesium ferrite at a flow rate of 1.0 liquid hourly space velocity. Air is present in the reaction mixture in an amount equivalent to 0.60 mol of oxygen per mol of butene. Steam is present in the reaction mixture in an amount of 30 mols of steam per mol of butene. The reaction temperature is approximately 450° C. Under these conditions, 61 mol percent of butene-2 is converted with the selectivity to butadiene being 92 mol percent of the butene-2 converted for a yield of butadiene of 56 percent.

EXAMPLE 29

Barium ferrite (Columbian Carbon Co. EG-4, lot 101, 261) is used as the catalyst. The barium ferrite has about 12 atoms of iron per atom of barium. The barium ferrite is coated on 4 to 8 mesh fused alumina pellets in an amount of roughly 30 percent by weight barium ferrite based on the total weight. Ethyl benzene is dehydrogenated at atmospheric pressure in a Vycor glass reactor $(36''\times 1''$ O.D.) having a 50 cc. catalyst bed supported on a 1" deep layer of $\frac{1}{4}\times\frac{1}{4}''$ O.D. Vycor Raschig rings. Ethyl benzene, oxygen, and steam and HBr are introduced into an adapter located on top of the glass reactor, and the effluent gases are passed through a cold-water condenser to remove most of the steam.

The mixture of ethyl benzene, oxygen, HBr and steam are fed to the reactor in an amount of 1.0 mol of oxygen, 20 mols of steam, and 0.075 mol of bromine per mol of ethyl benzene (calculated as $Br_2$). The LHSV is 0.3. Styrene is produced in good yields.

EXAMPLE 30

A strontium ferrite catalyst is formed as follows: 80.0 grams of strontium chloride and 48.7 grams of ferric chloride are dissolved in 350 cc of distilled water. A second solution is prepared by dissolving 100 grams of potassium hydroxide in 750 cc. of distilled water. A reddish brown slurry is obtained by adding the mixed chloride solution into the potassium hydroxide solution with stirring. The slurry was then dewatered by filtering and the coprecipitate is washed with distilled water until it was neutral. The mixture was dried in an oven at a temperature of 130° C. After drying, the black solid is reacted at 900° C. to form the strontium ferrite. The strontium ferrite is a magnetic black solid. Example 29 is repeated with the strontium ferrite being substituted for the barium ferrite. A high yield of styrene is obtained.

EXAMPLE 31

Example 30 is repeated with the exception that calcium ferrite is substituted for the strontium ferrite of Example 30. The calcium ferrite is formed according to the method described in Gmelin Handbuck Der Anorganischen Chemie, 59 B4-5, page 1071. Ferric oxide is used as a source of iron and the atomic ratio of the atoms of Fe to the atoms of Ca is 2 to 1. The temperature of reaction to form the ferrite is 1000° C. for a period of one hour. The calcium ferrite obtained is a slightly magnetic dark brown solid. The calcium ferrite is slurried in water to make a paste, dried, and the dried cake broken into lumps. A 6 to 8 mesh fraction is used as a catalyst.

EXAMPLE 32

A catalyst is prepared having magnesium ferrite modified with both phosphorus and silicon. The final catalyst consists of the same magnesium ferrite used in Example 8 together with two percent by weight $H_3PO_4$ and $SiO_2$. This composition is coated on inert alumina carriers, type AMC, size 4 to 5 mesh. Prior to operation, the reactor containing the catalyst is purged at room temperature with nitrogen and thereafter hydrogen is introduced at 500 cc. per minute (STP). The reactor in a hydrogen atmosphere is then held at 570° C. for a period of two hours. Thereafter the reactor is cooled to 370° C. and purged with methane. Next, the steam, butene-1 and air flows are begun. HCl gas is also fed to the reactor in an amount of 3.0 mols per mol of butene- 1. Butene-1 is fed at a rate of one liquid hourly space velocity. Steam is employed in an amount of 30 mols of steam per mol of butene-1 and oxygen is present in an amount of 0.75 mol of oxygen per mol of butene-1 fed as air. Chloroprene is produced.

EXAMPLE 33

A cadmium ferrite catalyst is formed as follows: 64.2 grams of cadmium oxide, 79.9 grams of ferric oxide and 74.6 grams of potassium chloride are thoroughly mixed in dry form. The mixture is then reacted in a furnace at 900° C. for a period of three hours. After cooling to room temperature, hot distilled water is used to extract the potassium chloride from the reacted mixture until the extract is free of chloride ion. A reddish brown cadmium ferrite solid is obtained. Using this catalyst and the reactor of Example 1, n-heptane is dehydrogenated to toluene utilizing 1.5 mols of oxygen per mol of n-heptane.

EXAMPLE 34

A catalyst is prepared containing 90 weight percent Columbian Carbon magnesium ferrite, type EG-1, and 10 percent by weight of $H_3PO_4$. The catalytic composition is coated onto 4 to 5 mesh inert carrier particles in an amount of 30 percent by weight of the total weight. After loading the catalyst into the reactor, the catalyst is maintained in a hydrogen atmosphere for two hours at a temperature of 510° C. Butene-2 is dehydrogenated at a flow rate of one liquid hourly space velocity, steam is included in the composition fed to the reactor in an amount of 30 mols of steam per mol of butene-2, and oxygen is present as air in an amount equivalent to 0.80 mol of $O_2$ per mol of butene-2. The maximum temperature in the reactor is about 540° C. After 48 hours of operation, the yield of butadiene-1,3 is 68 mol percent.

EXAMPLE 35

The catalyst utilized is a ferrite containing iron, magnesium and cobalt modified by phosphorus. 178 grams of yellow iron oxide and 32 grams of magnesium oxide are mixed in 700 ml. of distilled water, ball-milled for 16 hours and filtered. Cobalt nitrate hydrate, 29 grams, and 2.3 grams of magnesium chloride hydrate are dissolved in 50 ml. distilled water. This solution is added to the filtered mixture of oxides and the combination is stirred for 30 minutes. A heavy paste is obtained which is dried in an oven at 105° C. for 16 hours. The dried material is heated at 900° C. for 60 minutes in order to form the ferrite. After cooling, the ferrite composition is reslurried in distilled water, and $H_3PO_4$ is added in an amount equivalent to two percent by weight of 85 percent $H_3PO_4$ based on the weight of the ferrite. Alumina catalyst supports, 4 to 6 mesh AMC, are then added. The coated catalyst particles are then re-dried and loaded into a dehydrogenation reactor. A 10-inch catalyst bed is employed in a 1-inch diameter reactor tube. 2,3-dichlorobutane is dehydrogenated to chloroprene. The flow rate of 2,3-dichlorobutane was one liquid hourly space velocity. Steam is fed in an amount of 15 mols of steam per mol of 2,3-dichlorobutane, and oxygen is fed as air in an amount equivalent to 0.68 mol of $O_2$ per mol of 2,3-dichlorobutane.

EXAMPLE 36

The catalyst contains a combination of magnesium ferrite and zinc ferrite composition modified with phosphorus. The magnesium ferrite is the same type EG-1 used in some of the above examples. The zinc ferrite is Columbian Carbon Company Type EG-2 having x-ray diffraction peaks at d spacings within 4.83 to 4.89, 2.95 to 3.01, 2.51 to 2.57, 2.40 to 2.46, 2.08 to 2.14, 1.69 to 1.75, 1.59 to 1.65, and 1.46 to 1.52, with the most intense peak being between 2.95 to 3.01. The x-ray determinations are run with a cobalt tube. The catalyst is prepared by mixing 5 weight percent of the zinc ferrite with 95 percent by weight of the magnesium ferrite in an aqueous slurry of distilled water. To this composition is added two percent by weight of 85 percent $H_3PO_4$ aqueous solution based on the total weight of the zinc ferrite and magnesium ferrite. After this composition has been thoroughly mixed, alumina carrier, Type SA 5218, is added and the catalytic composition coated on the carrier. The carrier particles are 3/16 inch in diameter. After the catalyst is loaded into the reactor, hydrogen is passed through the reactor for about two hours with the catalyst temperature being about 500° C. Methyl isopropyl ketone is dehydrogenated to methyl isopropenyl ketone at a reactor temperature of 450° C. and with oxygen present in an amount of 0.6 mol and ammonium chloride present in an amount of 0.3 mol per mol of methyl isopropyl ketone.

EXAMPLE 37

A cobalt ferrite catalyst is formed in the following manner: 119.0 grams of cobaltous chloride and 135.2 grams of ferric chloride are dissolved in 500 cc. of distilled water. A second solution is prepared by dissolving 110 grams of sodium hydroxide in one liter of distilled wter. The mixed chloride solution is added slowly to the sodium hydroxide solution with stirring. A coprecipitate of cobaltous and ferric hydroxides is obtained. The slurry is then dewatered by filtering and washing with distilled water until it is neutral. The mixture is dried in an oven at a temperature of 110° C. After drying, the black solid is reacted in a furnace at a temperature of 900° C. for a period of one and one-half hours. Cobalt ferrite, a magnetic black solid, is obtained. Propionitrile is dehydrogenated to acrylonitrile. Oxygen is fed in an amount of 0.75 mol per mol of propionitrile and steam is utilized in an amount of 20 mols per mol of propionitrile. The liquid hourly space velocity is 1.0. The reactor temperature is 500° C.

According to this invention it has been found that the preferred catalysts exhibit a certain type of X-ray diffraction pattern. The preferred catalysts do not have as sharp X-ray diffraction reflection peaks as would be found, e.g., in a high crystalline material having the same chemical composition. Instead, the preferred catalysts of this invention exhibit reflection peaks which are relatively broad. The degree of sharpness of the reflection peak may be measured by the reflection peak band width at half height (W h/2). In order words, the width of the reflection peak as measured at one-half of the distance to the top of the peak is the "band width at half heighth". The band width at half heighth is measured in units of °2 theta. Techniques for measuring the band widths are discussed, e.g., in Chapter 9 of Klug and Alexander, X-ray Diffraction Procedures, John Wiley and Son, N.Y., 1954. The observed band widths at half heighth of the preferred catalysts of this invention are at least 0.16 °2 theta and normally will be at least 0.20 °2 theta.* For instance, excellent catalysts have been made with band widths at half heighth of at least 0.22 or 0.23 °2 theta. The particular reflection peak used to measure the band width at one-half heighth was the reflection peak having Miller (hkl) indices of 220. (See, e.g., Chapter of Klug and Alexander, ibid). The reason that materials which have relatively wide band width at one-half heighth is not fully understood. Furthermore, applicant does not wish to be limited to any theory of the invention in regard to the relationship between catalyst activity and crystallite size.

*The powder diffraction patterns were made with a Norelco constant potential diffraction unit type No. 12215/0 equipped with a wide range goniometer type No. 42273/0, cobalt tube type No. 32119, proportional counter type No. 57250/1; all coupled to the Norelco circuit panel type No. 12206/53. The cobalt K alpha radiation is supplied by operating the tube at a constant potential of 30 kilovolts and a current of 10 milliamperes. An iron filter is used to remove K beta radiation. The detector voltage is 1600 volts and the pulse height analyzer is set to accept pulses with amplitudes between 10 and 20 volts only. Slits used are divergence 1°, receiving 0.006 inches and scatter 1°. Strip chart recordings for identification are made with a scanning speed of ¼° per minute, time constant of 4 seconds and a full scale at $10^8$ counts per second. No correction is made for K $\alpha$ doublet or instrumental broadening of the band widths.

In the above description it was stated that preferred catalysts have X-ray reflection peaks within certain d spaces. An alternate way to define the reflection peaks of the preferred catalysts is by reference to the Miller (hkl) indices of the reflection peaks found. The preferred catalysts have a cubic structure and have the most intense reflection peak at the Miller (hkl) index of 311, and generally will have reflection peaks at (hkl) indices including the following: 220, 400, 422, 440 and 333 and/or 511. For the determination of these (hkl) indices, the materials are only scanned from 0° to 80° 2 theta. Other reflections within this range may also be present. Also, reflections outside the range scanned will normally be present.

The products of this invention have many known uses, as many of them are, e.g., commercial monomers such as acrylonitrile.

We claim:

1. A process for the oxidative dehydrogenation of dehydrogenatable organic compounds which comprises contacting an organic compound having at least one

grouping and having from 1 to 12 carbon atoms in vapor phase at a temperature of at least about 250° C. with at least about 0.20 mols of oxygen per mol of organic compound with a catalyst having as its main active constituent a crystalline structure of iron, oxygen and at least one metal element other than iron selected from the group consisting of Cu, Al, Cr, Ti, V, Mo, W, Na, Li, K, Sn, Pb, Sb, Bi, Ga, rare earth elements and mixtures thereof which is capable of forming a crystalline structure with iron and oxygen.

2. The process of claim 1 wherein the said catalyst is a ferrite.

3. The process of claim 1 wherein the said metal element other than iron is selected from the group consisting of metals having an ionic radius of from 0.5 and 1.1 angstrom units.

4. The process of claim 1 wherein the said metal elements other than iron are present in a total amount of from 0.05 to 2.0 atoms per atom of iron.

5. The process of claim 1 wherein the crystalline structure of said catalyst is of the face-centered cubic form.

6. The process of claim 1 wherein the crystalline structure of said catalyst is not in the most highly oriented form and wherein the crystalline structure has been formed at a temperature of less than 1150° C.

7. The process of claim 1 wherein the said organic compound is propionitrile.

8. The process of claim 1 wherein the said organic compound is a hydrocarbon.

9. The process of claim 1 wherein the said organic compound is normal butene.

10. The process of claim 1 wherein the process also contains a halogen selected from the group consisting of iodine, bromine, chlorine and mixtures thereof in an amount up to 0.09 mol of halogen per mol of organic compound.

11. The process of claim 1 wherein the ratio of said oxygen to said organic compound is from 0.2 to 2.5 mols of oxygen per mol of organic compound and the said temperature of dehydrogenation is from 375° C. to 750° C.

12. The process of claim 1 wherein the catalyst is chromium ferrite.

13. The process of claim 1 wherein the catalyst is a rare earth ferrite.

14. The process of claim 1 wherein the catalyst consists of from 30 to 90 weight percent of the total weight of iron and the said metal element(s) other than iron.

15. The process of claim 1 wherein the said crystalline structure is essentially $MeFe_2O_4$ with Me representing the said metal element(s) other than iron.

16. The process of claim 1 wherein the said catalyst comprises a ferrite containing a divalent metal selected from said group and a trivalent metal selected from said group.

17. The process of claim 16 wherein the said trivalent metal is selected from the group consisting of aluminum or chromium.

18. The process of claim 17 wherein the said metal elements other than iron are present in a total amount of from 0.05 to 2.0 atoms per atom of iron.

19. The process of claim 18 wherein said divalent metal has an ionic radius between 0.5 and 1.1 angstrom units.

20. The process of claim 17 wherein the said organic compound is a hydrocarbon.

21. The process of claim 20 wherein the said hydrocarbon is normal butene.

22. The process of claim 17 wherein the said organic compound is a hydrocarbon containing at least about 4 carbon atoms, the mixture additionally contains per mol of hydrocarbon about 5 to 30 moles of steam and from 0.35 to 1.2 moles of oxygen, the oxidative dehydrogenation is conducted at a temperature at least about 250° C. thereby producing a dehydrogenated hydrocarbon having the same number of carbon atoms as the said hydrocarbon.

23. A process for the oxidative dehydrogenation of dehydrogenatable organic compounds which comprises contacting an organic compound having at least one

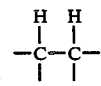

grouping and having from 2 to 12 carbon atoms in vapor phase at a temperature of at least about 250° C. with at least about 0.20 mols of oxygen per mol of organic compound with zirconium ferrite catalyst.

24. A process for the oxidative dehydrogenation of dehydrogenatable organic compounds contacting an organic compound having at least one

grouping and having from 1 to 12 carbon atoms in vapor phase at a temperature of at least about 250° C. with at least about 0.20 mols of oxygen per mol of organic compound with a catalyst consisting essentially of a crystalline structure of iron, oxygen and at least one metal element other than iron selected from the group consisting of Cu, Al, Cr, Ti, V, Mo, W, Na, Li, K, Sn, Pb, Sb, Bi, Ga, rare earth elements and mixtures thereof which is capable of forming a crystaline structure with iron and oxygen.

25. The process of claim 24 wherein the said crystalline structure is a ferrite structure.

26. The process of claim 24 wherein the said organic compound is butene.

27. A process for the oxidative dehydrogenation of dehydrogenatable organic compounds which comprises contacting a hydrocarbon compound having at least one

grouping and having from 2 to 12 carbon atoms in vapor phase at a temperature of at least about 250° C. with at least about 0.20 mols of oxygen per mol of organic compound with a catalyst consisting essentially of a ferrite of iron and at least one element selected from the group consisting of Cu, Al, Cr, Ti, V, Mo, W, Na, Li, K, Sn, Pb, Sb, Bi, Ga, Ce, Th, other rare earth elements and mixtures thereof.

28. A process for the oxidative dehydrogenation of organic compounds having from 2 to 12 carbon atoms and being selected from the group consisting of nitriles, amines, alkyl halides, ethers, esters, aldehydes, ketones, alcohols, acids, alkyl aromatic compounds, alkyl heterocyclic compounds, cycloalkanes, alkanes and alkenes which comprise contacting said organic compound in vapor phase at a temperature of at least about 250° C. with a catalyst consisting essentially of a ferrite of iron and at least one member other than iron selected from the group consisting of Cu, Al, Cr, Ti, V, Mo, W, Na, Li, K, Sn, Pb, Sb, Bi, Ga, rare earth elements and mixtures thereof.

29. The process of claim 28 wherein the said organic compound is a hydrocarbon.

30. The process of claim 28 wherein the ferrite is of the approximate formula $MeFe_2O_4$ wherein Me represents divalent metals having an ionic radius between 0.5 and 1.1 angstrom units.

31. The process of claim 28 wherein the ferrite is of the approximate formula $MeFe_2O_4$ wherein Me represents a combination of ions having an average valency of two.

32. The process of claim 28 wherein the said catalyst is selected from the group consisting of cupric ferrite, cuprous ferrite, lithium ferrite, potassium ferrite, sodium ferrite, lead ferrite, silver ferrite, zirconium ferrite, rare earth ferrites and mixtures thereof.

* * * * *